United States Patent [19]

Martin et al.

[11] 4,326,082

[45] Apr. 20, 1982

[54] USE OF AQUEOUS TRIETHYLAMINE/PHOSPHORIC ACID SALT SOLUTIONS TO EXTRACT WATER AND TRIETHYLAMINE FROM SOLUTIONS THEREOF IN ORGANIC SOLVENTS

[75] Inventors: Patrick H. Martin, Danville; Stephen L. Michaels, Oakland, both of Calif.

[73] Assignee: The Dow Chemical Company, Midland, Mich.

[21] Appl. No.: 137,653

[22] Filed: Apr. 7, 1980

[51] Int. Cl.³ .................................................. C07C 85/26
[52] U.S. Cl. .................................................. 564/497
[58] Field of Search ................................. 564/497, 499

[56] References Cited

U.S. PATENT DOCUMENTS

| | | | |
|---|---|---|---|
| 3,470,252 | 9/1969 | Doyle et al. | 564/499 X |
| 3,855,298 | 12/1974 | Bathellier et al. | 564/499 |
| 3,864,402 | 2/1975 | Swanson et al. | 564/499 X |
| 4,152,219 | 5/1979 | Newton et al. | 564/499 X |

*Primary Examiner*—Robert V. Hines
*Attorney, Agent, or Firm*—R. R. Stringham

[57] ABSTRACT

Triethylamine and water are simultaneously removed from solutions in organic solvents, by liquid/liquid extraction with concentrated aqueous solutions of $(C_2H_5)_3N \cdot H_3PO_4$ which preferably contain free phosphoric acid as well. Upon heating of the resulting extract, the water and amine taken up are boiled off and the extractant regenerated. The method is of particular value in the preparation of aqueous coating compositions comprising reaction products of polyether epoxides and $H_3PO_4$ in organic media. The reaction product is salified with triethylamine in excess, in the presence of added water. The organic solvent is boiled off, together with the excess amine and some of the water, to form an aqueous dispersion of the salified product and a distillate which can be processed by the method of the invention. The recovered solvent, water and amine may be recycled.

9 Claims, 1 Drawing Figure

USE OF AQUEOUS TRIETHYLAMINE/PHOSPHORIC ACID SALT SOLUTIONS TO EXTRACT WATER AND TRIETHYLAMINE FROM SOLUTIONS THEREOF IN ORGANIC SOLVENTS

BACKGROUND OF THE INVENTION

In preparing the coating compositions referred to in the Abstract (see U.S. Pat. No. 4,164,487), amines other than triethylamine can be employed. In any case, however, it is highly desirable to introduce the amine in excess of the amount required to salify enough of the P—OH groups in the reaction product to render it dispersible in water. Thus, the overhead formed by boiling off the reaction medium only not includes water but also the excess amine—which must be recovered—for both economic and environmental reasons.

In most methods of amine extraction found in the literature, the amine component of a fluid stream is adsorbed on a solid. Adsorption on activated carbon, for example, is essentially irreversible but reversible adsorption occurs when the solid is an ion-exchange resin (as described by B. S. Fee and M. G. Rogers; *Separation of Amines by Ligand Exchange;* Parts I–IV. *Analytica Chimica Acta;* 32 (1965) p. 101, 33 (1965) pp. 84–90, and 37 (1967), pp. 102–111). No disclosure of liquid/liquid amine extraction or of simultaneously extracting more than incidental amounts of water was found in the literature.

Triethylamine is preferred for other reasons in the manufacture of the above-referred-to coating compositions and, fortunately, has proven to be particularly amenable to recovery by the process of the present invention.

The only references found to uses of triethylamine phosphate salts are in U.S. Pat. No. 2,917,481—which discloses the use of such salts as corrosion inhibitors—and in U.S. Pat. No. 3,300,693, which is directed to the use of quaternary ammonium salts as dielectric fluids.

OBJECTS OF THE INVENTION

The primary object of the present invention is to provide a method of removing amines from solutions thereof in organic solvents which makes possible economic recovery and recycling of the amines and the solvents.

An ancillary object is to provide such a method in which, when said solutions are wet, at least a substantial proportion of the water is simultaneously removed with the amines.

A further object is to provide a method of removing amines from process streams which does not require the use of solids.

An additional and highly important object is to facilitate closed system processing, i.e., processing in a system from which no waste streams are discharged.

Another object is to provide a method of amine (and water) recovery which is readily carried out in a continuous manner.

Still other objects will be made apparent to those knowledgeable in the art by the following specification and claims.

SUMMARY OF THE INVENTION

Broadly, the invention is the use of aqueous solutions of amine phosphates to remove amines from solutions thereof in organic solvents, by liquid/liquid extraction.

Figure 1:
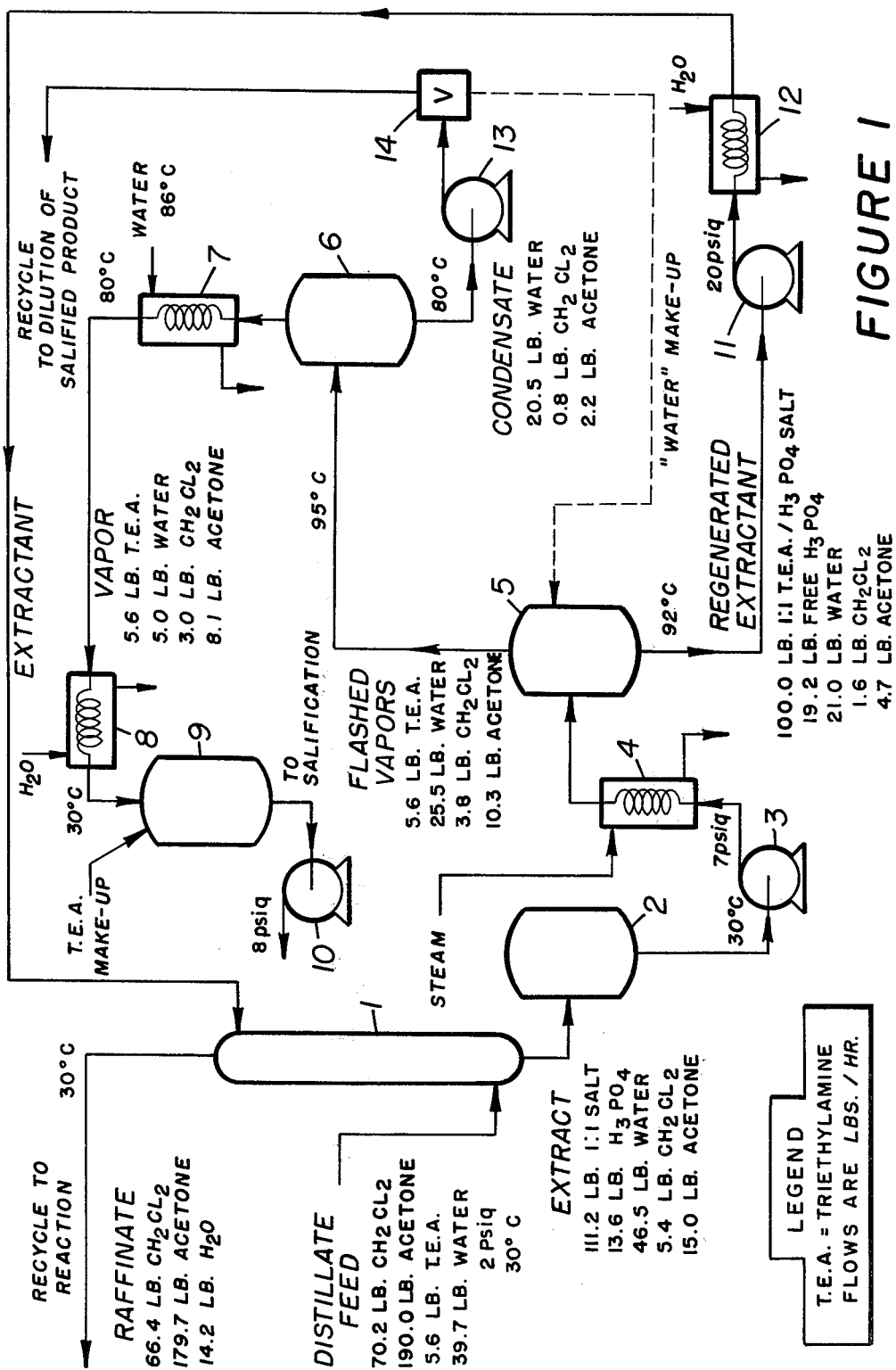
FIG. 1 is a flow sheet for the portion of a closed, continuous resin-dispersion manufacturing process in which the present invention is embodied as a counter-current extraction operation. See Example 4.

More precisely, the present invention may be defined as the process for removing an amine from a solution thereof in an organic solvent which comprises intimately contacting said solution with an extractant which is an aqueous solution of a 1:1 salt of an amine (preferably the same amine) with orthophosphoric acid, and then separating the organic and aqueous phases (the resultant raffinate and extract).

In a preferred embodiment of the invention, the amine solution also contains water, of which at least a substantial proportion is coextracted with the amine by the salt solution.

Advantageously, the salt solution also contains up to 1 mole of free $H_3PO_4$ per mole of the 1:1 amine phosphate.

DETAILED DESCRIPTION

Suitable feed solutions (solutions of amines in organic solvents) for the practice of the invention are those in which:

(a) the amine to be recovered will form a water-soluble associated product with the amine phosphate and/or phosphoric acid in the aqueous extractant; preferably the extracted amine can readily be liberated by heating the extract to a higher temperature than that at which the extraction is carried out;

(b) the organic solvent is essentially inert to the amine and to the extractant, i.e., it must not detrimentally react with the same to an intolerable extent, under the extraction conditions employed;

(c) the solvent also should not be freely miscible with the extractant, at the contemplated extraction temperature. That is, the solvent should not be soluble in the extractant to such an extent that the extract will contain more than about 15 mole percent of the solvent. Preferably, the total content of organic solvents will not exceed about 10 mole percent;

(d) the water content of the feed is not so high that a distinct phase separation between the raffinate and extract does not result or the raffinate contains any substantial proportion of the $H_3PO_4$ originally present (as such or in salt form) in the extractant.

The process of the invention has not been actually carried out with amines other than triethylamine ("T.E.A."). However, it is well known that amines in general form water-soluble salts with phosphoric acid and the dissociation equilibria of such salts in aqueous solution would be expected to be similarly temperature dependent.

Although T.E.A. is water-miscible at temperatures below 18.7° C., it exhibits a low solubility in water at temperatures above 18.7° C. Consequently, solubility of the amine in water (as distinguished from "solubility" in aqueous solutions of amine phosphates and/or phosphoric acid) does not appear to be an essential requirement.

Those skilled in the art will be well able to determine whether any given candidate amine meets the criteria set out above and such procedural variations as may be required to accommodate the differences in properties between T.E.A. and other amines will be apparent to them. Consequently, it does not appear that any useful purpose would be served by cataloging herein specific such other amines.

Similarly, the process of the invention has not actually been carried out with feed solutions in which the solvent component was other than a mixture of methylene chloride and (predominantly) acetone. However, no reason is seen why the process should not work as well or better with other solvents meeting the criteria set out above—particularly those solvents which, unlike acetone per se, are not water-miscible. Such procedural modifications as might be necessary in order to practice the present invention with feeds comprising such other solvents will be apparent to those skilled in the art. Accordingly, no point is seen in cataloging specific such other solvents. However, methyl ethyl ketone may be mentioned as a solvent found particularly useful in forming good aqueous dispersions of some (salified) epoxide/$H_3PO_4$ adducts which are less amenable to dispersion when dissolved (together with water) in acetone or acetone/methylene chloride (the solvent then being removed).

The preferred solvent component, at least in T.E.A. feed solutions, is a mixture of acetone and methylene chloride in which the proportion of acetone is within the range of from about 65 to about 80 weight percent. Particularly preferred are such mixtures in which the proportion of acetone is within the range of from about 72 to about 74 weight percent.

Suitable extractant solutions for the practice of the invention are aqueous amine phosphate solutions comprising water and a (water-soluble) 1:1 salt of an amine and $H_3PO_4$. Partially "loaded" extracts having overall T.E.A. (for example) to $H_3PO_4$ mole ratios of less than 2 are capable of taking up more T.E.A. Preferably, however, the amine to acid ratio is less than 1, i.e., free phosphoric acid is present with the 1:1 salt.

The amine component of the salt preferably is—but does not have to be—the same as the amine to be extracted. If it is not the same and the recovered amine is recycled to the source of the feed solution, the return stream will contain both amines (except in the unlikely circumstance that the salt of the extracted amine decomposes completely at a temperature below that at which the rate of decomposition of the other amine salt becomes substantial).

The extractant may also comprise any other materials which do not detrimentally effect its usefulness in the process to an intolerable degree. The solvent component of the feed may have some solubility in the extractant (as in the case of acetone, for example), but this does not necessarily pose any difficulty, particularly in a cyclic process in which the extracted solvent can be recovered and reused. In the embodiment of the invention presently of most interest, acetone/$CH_2Cl_2$ happens to be co-extracted, to a limited extent, with T.E.A. and water. It is not necessary to remove all of the solvent from the extract in order to regenerate the extractant. Thus, some of the solvent is left in the extractant and the amount of solvent taken up during the extraction is less than if all of the solvent had been removed from the extract.

The key extraction process parameters are temperature, mixing and disengagement times, the relative amounts of salt, water and free acid in the extractant, the volume ratio of feed to extractant solutions and the feed solution contents of water and amine.

Temperature

Operation at ordinary temperatures (20°–25° C.) results in somewhat lower amine contents in the extract than operation in the vicinity of 0° C. —at least when no free acid is included in the extractant. As the temperature is increased above 25°, a progressively more substantial decrease in amine content results and at a temperature of 80° C., the equilibrium is strongly shifted towards salt decomposition, rather than salt formation. It is preferred to carry out the extraction at temperatures of 25° or less. Although temperatures down to those at which solids start to form (in the vicinity of −5° C., for example) are considered operable, the benefits realized by going to temperatures substantially lower than 20° C. will generally not be such as to justify the cost of the cooling required. The preferred extraction temperature range thus is from about 20 to about 25° C.

Contacting and Settling Times

The time required to ensure equilibration between the two phases in the extraction will vary with the degree of mixing attained, the temperature and the initial compositions of the feed and extractant, according to principles familiar to those skilled in the art. Although the minimum contact time required to effect a satisfactory approach to an equilibrium condition in a given system can be estimated by known methods, empirical laboratory tests will generally be relied on as well and these can readily be carried out without resort to further invention. Similarly, the time required to effect a satisfactory degree of disengagement between the raffinate and extract will depend on factors which are well understood and may be pin-pointed by bench tests in known types of settling means.

Example 3 herein includes flow rates and zone dimensions from which representative contacting and settling times may be estimated.

Extractant Component Proportions

The presence of the 1:1 amine/$H_3PO_4$ salt in the extractant is essential to efficient extraction of the amine. If extraction is attempted using phosphoric acid alone, acid transfer to (and salt formation in) the feed solution may result. Furthermore, in order to operate in a cyclic manner, all of the salt in the extract will have to be decomposed and this will require substantially higher temperatures. Also, if efficient co-extraction of water is desired, a substantial proportion of the salt which will be present in the extract must be present in the extractant when charged to the extraction.

It is not necessary to include any free acid in the extractant because (in the presence of enough water) the 1:1 salt molecules present can be made to take up another molecule of the amine, each, and the resulting 2:1 salt molecules can be thermally decomposed in aqueous solution to regenerate the 1:1 salt and liberate the extracted amine. However, in order to achieve a maximum amine recovery (per pass) from the feed solution, it is essential to include at least some free acid in the extractant. Theoretically, there is no limit to the mole ratio of free acid to 1:1 salt in the extractant. However, ratios above 1 (an overall $H_3PO_4$ to amine ratio of 2) are not considered very practical. The higher the ratio, the more likely that some of the acid will report in the raffinate. Another drawback is that the ability of the extractant to take water out of the feed solution will decrease as the salt to acid ratio drops. Also, in order to operate in a cyclic mode, the proportion of the salt (1:1) in the extract which must be decomposed in order to regenerate the extractant goes up with the acid to salt ratio. Preferably, the free acid to 1:1 salt mole ratio is from about 0.2 to about 0.5.

The extraction could be carried out with an extractant comprising undissolved particles of the salt, in order to extract more water from a very wet feed solution, for example. However, this ordinarily will not be worth the handling complications involved and will be counterindicated for a cyclic process, which would require a substantially higher energy consumption for additional water removal from the extract. Thus, more of the salt than is required to provide a saturated solution will ordinarily not be present in the extractant. On the other hand, the use of extractants so dilute that the salt to water mole ratio is less than 0.1 is not contemplated for the general practice of the invention; the efficiency of water extraction would be expected to drop off very rapidly at lower ratios. Preferably, the 1:1 salt to water mole ratio is within the range of from about 0.2 to about 0.5.

Volume Ratio of Feed to Extractant

In view of the fact that an increase in feed to extractant volume ratio from 4 to 11 only lowered T.E.A. and water extraction efficiencies (in batch extractions employing no free acid) from 81% and 58%, respectively, to 75% and 55%, it is considered that the utility of the process extends at least to feed to extractant volume ratios as high as 25 to 1. However, ratios within the range of from about 2 to about 8 are preferred.

Feed Component Proportions

Theoretically, the extraction method can be practised with feed solutions in which there are more amine than solvent molecules—provided each volume of the feed is contacted with at least several volumes of the extractant and severe phase disengagement problems are not encountered. However, an advantage of the present process over conventional separation methods (such as fractional distillation) is that high separation efficiencies can be attained even though the amine content of the feed solution is quite low to start with. Advantageously, the amine content in the feed is not in excess of 5 mole percent. Preferably, the feed contains a total of 2 mole percent or less of amines. On the other hand, processing of solutions containing less than about 0.001 mole percent of amines is considered impractical.

The presence of a separate aqueous phase in (admixture with) the feed solution is not contemplated. Any such aqueous phase can be separated prior to the extraction step. (If the amine is T.E.A. and the phases are separated at a temperature above 18.7° C., not much of the amine will report in the aqueous phase; the solubility of T.E.A. in water at 30° C. is only about 5 wt. %.) Consequently, the maximum amount of water introduced to the extraction with the amine and a water-immiscible solvent will be that present when the solvent/amine solution is saturated with water. If the solvent is a solvent mixture comprising water-immiscible and water-miscible solvents, the maximum water content ordinarily will be that just insufficient to cause phasing out of the water-immiscible solvent. If the solvent is perfectly water-miscible, the maximum tolerable water content in the feed solution ordinarily will be that at which analytically detectable amounts of phosphorus begin to report in the raffinate.

The limiting water content of the feed solution in each of the preceding three cases of course can readily be determined for any given solvent/amine combination by a few simple bench tests. However, as a guide, it may be noted that one volume of a feed solution containing 13 wt. % of water and otherwise consisting of T.E.A. (2 wt. %) and acetone/$CH_2Cl_2$ (73/27 wt. ratio), when extracted with as few as about 0.5 volumes of an extractant consisting of 1.1 T.E.A. $H_3PO_4$ (64.6 wt. %), free $H_3PO_4$ (12.4 wt. %), acetone/$CH_2Cl_2$ (4.1 wt. %) and 18.3 wt. % of water, yields a raffinate consisting of acetone/$CH_2Cl_2$ (95 wt. %) (5 wt. %).

Modes of Feed/Extractant Contact

The extraction may be operated as a single or multiple contact process, either batchwise or continuously and—in multiple contact—in either co-current or counter-current flow.

The presently preferred mode of carrying out the extraction is continuous, counter-current extraction (as part of a continuous, closed process for manufacturing water dispersible, neutralized adducts of $H_3PO_4$ with polyether epoxide resins). A representative such process (somewhat simplified) comprises the following steps.

a. A polyhydroxy, polyether epoxide resin is reacted with phosphoric acid in a relatively low-boiling organic reaction medium. An amine, in excess over the amount required to neutralize (salify) the P-OH groups in the resultant adduct, is added to the reaction mixture, which is then diluted with water and stripped of solvent to form an aqueous dispersion of the salified adduct.

b. The solvent overhead is condensed as two cuts, the lower boiling (fore) cut consisting largely of the reaction medium but also having a substantial water content and comprising a small amount of the amine. (The higher boiling cut is largely water but includes some solvent and the rest of the excess amine charged to the neutralization. This cut is recycled to the neutralization step.)

c. The forecut is counter-currently contacted with a concentrated aqueous solution of the 1:1 salt of the amine with phosphoric acid, comprising less than 1 mole of the free acid per mole of the salt. The resulting raffinate is returned to the reaction step (with or without being dried first, depending on the water content that can be tolerated during the acid/epoxide reaction).

d. The extract is preheated to the temperature required to decompose that portion of its salt content which was formed during the extraction, and then flashed. The bottoms product from the flash is recycled, as extractant, to the extraction and the overhead—which is predominantly solvent (reaction medium) but includes substantial amounts of water and the amine, is recycled to the neutralization/dilution step.

EXAMPLES

The following examples are for purposes of illustration and are not to be construed as limiting the scope of the present invention in a manner inconsistent with the claims appended to this specification.

EXAMPLE 1

Single-stage batch extractions of T.E.A. and water from solutions thereof in acetone/$CH_2Cl_2$ (~66/34 wt. ratio), using a 60 wt. % aqueous solution of 1/1 or 1.13/1 T.E.A./$H_3PO_4$ as the extractant.

A synthetic feed (distillate) and a (1:1T.E.A./$H_3PO_4$) extractant solution having the following compositions were made up.

| Component | Wt. Percent in | |
|---|---|---|
| | Feed | Extractant |
| Acetone | 62.20 | — |
| $CH_2Cl_2$ | 31.60 | — |
| Water | 4.60 | 40.0 |
| T.E.A. | 1.60 | 30.96 |
| o-$H_3PO_4$ (100%) | — | 29.04 |

In tests 1 and 2 (Table 1 below), the extractant had the above composition but in test 3 the salt solution comprised 1.13 moles of T.E.A. per mole of $H_3PO_4$, to simulate a regenerated extract (see regeneration test results below).

The tests were carried out by mixing the distillate and extractant for 5 minutes in a round-bottomed flask at the volume ratios and temperatures given in the Table. The phases were allowed to disengage and separated. The residual T.E.A. contents in the raffinates were determined by titration with aq. HCl. The water, $CH_2Cl_2$ and acetone contents of the raffinates and extracts were measured by gas chromatography. The total amount of T.E.A. present (as the salt) in the extract was determined by titration with tetrabutyl ammonium hydroxide. All other concentrations were arrived at from component mass balances.

TABLE 1
RESULTS OF SINGLE STAGE BATCH EXTRACTIONS

| Run | Temp. (°C.) | Volume Ratio[1] | Wt. % in Raffinate T.E.A. | Wt. % in Raffinate $H_2O$ | Salt Stoichiometric Ratio[2] Extractant In | Salt Stoichiometric Ratio[2] Extract Out | Extraction Efficiencies[3] T.E.A. % | Extraction Efficiencies[3] $H_2O$ % | Extraction Efficiencies[3] Acetone % |
|---|---|---|---|---|---|---|---|---|---|
| 1 | 20 | 25.3 | 0.99 | 1.97 | 1.01 | 1.46 | 40.11 | 58.92 | 0.71 |
| 2 | 0° C. | 10.7 | 0.41 | 2.18 | 1.01 | 1.36 | 75.36 | 54.58 | 0.33 |
| 3 | 0° C. | 4.16 | 0.34 | 2.11 | 1.13 | 1.31 | 80.50 | 57.78 | 2.41 |

[1]Volume feed per volume extraction solution.
[2]Moles triethylamine per mole phosphate.
[3]Percent of available component extracted from feed.

The higher efficiency of amine extraction in runs 2 and 3, vs. run 1, is believed due to both the lower extraction temperature and the lower feed to extractant ratios.

It is evident from Table 1 that more than one stage is required in order to attain really low raffinate amine contents. Based on the extraction efficiencies given above, estimated raffinate concentrations of T.E.A., acetone and water after each of five successive, ideal stages of extraction in a standard cross-current scheme of contacting are given for each of tests 1-3 in Table 2 below. The calculations involved assume a 10:1 feed-/extractant ratio and fresh extractant at each stage.

TABLE 2
ESTIMATED RAFFINATE CONCENTRATIONS IN WEIGHT PERCENT AFTER EXTRACTION THROUGH SEVERAL STAGES

| | NUMBER OF EQUILIBRIUM CROSS-CURRENT STAGES | | | | |
|---|---|---|---|---|---|
| | (1) | (2) | (3) | (4) | (5) |
| Run 1 | | | | | |
| T.E.A. | 0.958 | 0.574 | 0.344 | 0.206 | 0.123 |
| WATER | 1.89 | 0.776 | 0.319 | 0.131 | 0.054 |
| ACETONE | 61.7 | 61.3 | 60.8 | 60.4 | 60.0 |
| Run 2 | | | | | |
| T.E.A. | 0.394 | 0.097 | 0.024 | 0.006 | 0.001 |
| WATER | 2.09 | 0.949 | 0.431 | 0.196 | 0.089 |
| ACETONE | 62.0 | 61.8 | 61.6 | 61.4 | 61.2 |
| Run 3 | | | | | |
| T.E.A. | .312 | .061 | .012 | .002 | $4.51 \times 10^{-4}$ |
| WATER | 1.94 | 0.820 | 0.346 | 0.146 | 0.062 |
| ACETONE | 60.7 | 59.2 | 57.8 | 56.4 | 55.1 |

A regeneration test was carried out as follows. An attempt was made to prepare, as a synthetic extract, a 55 wt. % aqueous solution of the 2:1 T.E.A./$H_3PO_4$ salt. However, at this water ratio, 0.29 moles of T.E.A. per mole of the acid remained undissolved as a separate phase (which was removed). The salt solution (1.71 moles of T.E.A./mole $H_3PO_4$; 50 wt. %) was stripped, at atmospheric pressure, to a pot temperature of 100° C. The T.E.A./$H_3PO_4$ mole ratio in the bottoms was found to be 1.13/1 and no further amine release occurred on continued heating at 100° C. The condensed overhead separated into two phases. The lighter phase analyzed for 85 wt. % T.E.A./15% water and could be used for the neutralization of epoxide/$H_3PO_4$ adduction mixture. The lower phase was a 6 wt. % solution of T.E.A. in water and could be used for the initial dilution of such a mixture with water.

EXAMPLE 2

Multi-stage batch extraction of wet acetone/$CH_2Cl_2$ amine solution with 1:1 T.E.A./$H_3PO_4$ solutions.

Batch extraction experiments modeling a countercurrent extraction column were used to obtain equilibrium data. "Distillate feed" and extractant were prepared having the compositions to be used in an actual column. Separatory funnels, each representing one stage in an extraction column, were numbered 1 through n. Using a ten-to-one volume ratio of feed to extractant, the solutions were mixed for 15 minutes at room temperature, then allowed to separate as equilibrated phases. The extract from this first extraction was drawn off and stored. The raffinate was placed in flask number "n−1", then fresh extractant was added, maintaining the 10:1 volume ratio. This solution was then stirred and separated as before. The extract from this separation was placed in flask number "n" and treated with the appropriate amount of feed solution. The raffinate phase was placed in flask number "n−2" and treated as before. This procedure was repeated until all final raffinate and extract phases were obtained. The number of extractions required to obtain the desired quality of raffinate should also be the number of ideal stages in a counter-current column. Data from this experiment, in which only 12 extractions were done, is presented in Table 3.

The results show that after 6 extractions the amine level was reduced from 1.7 wt. % T.E.A. to 0.005 wt. % T.E.A. It was concluded from these experiments that a column equivalent to five ideal stages would be adequate for reducing the amine level below 0.01 weight percent.

The weight percents of acetone, $CH_2Cl_2$, water and T.E.A. in the distillate feed were 62.40, 23.10, 12.80 and 1.70, respectively. The extractant was a 60 wt. % aqueous solution of the 1:1 salt.

TABLE 3
COUNTER-CURRENT MULTI-STAGE BATCH EXTRACTIONS WITH 1:1 T.E.A./$H_3PO_4$ SOLUTION

| SAMPLE** | COMPOSITION T.E.A. | WT. % WATER | PERCENT OF ORIGINAL T.E.A. REMOVED |
|---|---|---|---|
| INITIAL | 1.10 | 4.70 | |
| R-6-1 | 0.56 | 3.64 | 49.1 |
| R-5-1 | 0.23 | 3.64 | 79.27 |
| R-4-1 | 0.06 | 3.84 | 94.6 |
| R-3-1 | 0.018 | — | 98.36 |
| R-2-1 | 0.006 | 4.155 | 99.45 |
| R-1-1 | 0.005 | 4.555 | 99.55 |
| R-6-2 | 0.79 | 3.75 | 28.18 |
| R-5-2 | 0.56 | 3.55 | 49.09 |
| R-4-2 | 0.30 | 3.57 | 72.73 |
| R-3-2 | 0.17 | 3.60 | 84.55 |
| R-2-2 | 0.037 | 4.973 | 96.64 |
| R-1-2 | 0.01 | 4.19 | 99.09 |

**Notation Example: R-6-1:
R—raffinate phase
6—stage (Extraction) number
1—First sample of distillate feed

EXAMPLE 3

Several runs were made to evaluate different types of contacting means for continuous multi-stage (counter-current) extraction of T.E.A. and water from acetone/$CH_2Cl_2$ with 1:1 T.E.A./$H_3PO_4$ solutions. The feed solution was pumped through a flowmeter and up through an extraction column which was provided with seven vertically spaced sampling ports. The ascending feed was contacted in the column by a descending stream of extractant solution pumped through another flowmeter to the top of the column. The extract was drained from the column into a holding tank and the raffinate flowed out of the column, through a line equipped with a sampling port, to another holding tank.

The extraction column was a 44-inch length of 2-inch industrial glass pipe, fitted with seven 8-mm O.D. glass nipples (sampling ports) placed at 5-inch intervals along its length. Three different types of contacting means were tested in the column: a mixer-settler apparatus, a "rug roll" of polyethylene mesh and Raschig rings.

The mixer-settler was of a conventional type. Fourteen annular TEFLON ® plates are mounted at 2-½" intervals, by friction fit, on three 3/16" stainless steel, vertical rods inserted through holes in the plates and resting on the bottom of the column. The annular plates have an outer diameter of 1-¾" and an inner diameter of ¾" and define alternating mixing and settling zones.

Seven "paddle wheel" mixers are friction fit (in the mixing zones) at 4" intervals on a motor-driven, ⅜" stainless steel center shaft extending through a seal in the column top. Each wheel is 1" in diameter and has six ¼"×⅜" fins or "paddles".

The polyethylene contacting means was a 20"×34" piece of METEX ® mesh, which was rolled up to form a 2"×34" cylinder and pushed into the column.

The Raschig rings were dry-packed into the column to a depth of 22" above a ¼"×2" diameter TEFLON ® plate in which 27, ⅛" diameter holes had been drilled.

The compositions of the feed solutions used, the flow rates employed and the raffinate compositions are given for three runs in Table 4.

When the contacting means was the mixer/settler system, both the feed and the extractant were introduced to the column (bottom and top, respectively) at the pre-selected flow rates given in the Table. Agitation was started when the uppermost paddle wheel was submerged and was continued at a constant r.p.m.

In the packed column runs, the column was filled with extractant and then the feed flow was started. Thereafter the flows were regulated to maintain the level of the interface between the two phases essentially constant.

For all three runs, the extraction temperature was 27° C. and the extractant consisted of a 60 wt. % aqueous solution of the 1:1 T.E.A./$H_3PO_4$ salt (and 0.003 moles of free $H_3PO_4$ per mole of the salt).

Run 1 was carried out using the mixer/settler system, at 364 r.p.m. The polyethylene packing was used in run 2 and the Raschig rings in run 3.

TABLE 4
CONTACTING-MEANS EVALUATION RUNS

| RUN | FEED COMPONENT | WT. % | FLOW RATE (ML/MIN) FEED | EXTRACTANT | RAFFINATE COMPOSITION WT. % T.E.A. | WT. % WATER |
|---|---|---|---|---|---|---|
| 1 | ACETONE | 62.40 | 50 | 5 | 0.1 | 8.0 |
|   | METHYLENE CHLORIDE | 23.10 | | | | |
|   | WATER | 12.80 | | | | |
|   | TEA | 1.70 | | | | |
| 2 | ACETONE | 63.10 | 71 | 7.1 | 0.014 | 3.59 |
|   | METHYLENE CHLORIDE | 31.90 | | | | |
|   | WATER | 3.50 | | | | |
|   | TEA | 1.50 | | | | |
| 3 | ACETONE | 62.27 | 30 | 3 | 0.046 | 3.06 |
|   | METHYLENE CHLORIDE | 31.61 | | | | |
|   | WATER | 4.85 | | | | |

TABLE 4-continued

| | | CONTACTING-MEANS EVALUATION RUNS | | | | |
|---|---|---|---|---|---|---|
| | FEED | | FLOW RATE (ML/MIN) | | RAFFINATE COMPOSITION | |
| RUN | COMPONENT | WT. % | FEED | EXTRACTANT | WT. % T.E.A. | WT. % WATER |
| | TEA | 1.27 | | | | |

NOTE:
Run 1 was a mixer-settler run, while 2 and 3 were packed bed runs.

It is evident from Table 3 that effective amine and water removal can be attained at ordinary ambient temperatures by extraction with a solution of the 1:1 salt in a multi-stage contacting scheme. The highest degree of amine removal was experienced with the packed beds—particularly with the polyethylene mesh packing. However, channeling is believed to have occurred in run 2 (witness the anomalous water "extraction" results). In terms of water removal or conjoint water/amine removal, the Rashig ring bed gave the best results. The extractant "turnover" in run 3 perhaps could have off to ensure complete recovery of the extracted T.E.A. is in excess of the amount of water taken up in the extraction. Under the particular conditions and with the particular feed and extractant compositions employed in this example, this is not necessary (barring operating upsets requiring correction).

The solvent component of the distillate feed consists of acetone/$CH_2Cl_2$ in a 73/27 weight ratio and the mole % compositions of the streams entering the leaving the extraction column are as given below in Table 5 (which also includes the volume flow rates of those streams).

TABLE 5

| STREAM | FLOW RATE GPM[1] | MOLE PERCENT OF | | | | | |
|---|---|---|---|---|---|---|---|
| | | ACETONE | $CH_2Cl_2$ | WATER | T.E.A. | T.E.A./$H_3PO_4$ 1:1 SALT | FREE $H_3PO_4$ |
| FEED | 0.65 | 51.43 | 13.01 | 34.70 | 0.87 | — | — |
| EXTRACTANT[2] | 0.23 | 4.12 | 0.97 | 59.39 | — | 25.55 | 9.97 |
| RAFFINATE | 0.56 | 66.32 | 16.77 | 16.92 | — | — | — |
| EXTRACT[3] | 0.32 | 7.16 | 1.78 | 71.71 | — | 15.49 | 3.86 |

NOTES:
[1]Gallons per minute.
[2]Salt content 68.26 wt. %.
[3]Salt content 58.01 wt. %.

been better; the amine removal was excellent, early in the run, but decreased subsequently.

EXAMPLE 4

Continuous, counter-current extraction with aqueous solution of 1:1 T.E.A./$H_3PO_4$ salt and free $H_3PO_4$; raffinate and extract worked-up for recycle of solvent, amine and water.

This example illustrates the mode of practising the invention presently considered best. The suitability of the extraction method for inclusion in a cyclic, overall epoxide esterification and salification process is shown.

Referring to FIG. 1, 305.5 parts by weight per hour of the distillate feed and 146.5 parts/hour of the extractant are charged to an extraction column 1, containing a 4"×9' non-random, packed bed of Koch, stainless steel FLEXI-PACK ®, equivalent to at least six ideal extraction stages. The raffinate is taken off at a rate of 260.3 parts per hour and the extract—191.7 parts/hour—is passed through an accumulator tank 2 and a pump 3 to a heater 4, where it is raised to a temperature of 95° C., and is then flashed at atmospheric pressure in a flash vessel 5. The flashed vapors (45.2 parts/hour) are passed to a water separator 6 fitted with a partial condenser 7 through which hot (86° C.) water is also passed (on the shell side). The vapors (21.7 parts/hour) exiting from the partial condenser are liquified in water-cooled condenser 8, combined with make-up T.E.A. in accumulator 9 and recycled to the salification step by pump 10. The condensate (23.5 parts/hour) drained from vessel 6 is pumped by pump 13 through a porportioning valve 14 (which permits water return to vessel 5 if needed) and is recycled as noted. The regenerated extractant is withdrawn from vessel 5 and pumped by pump 11 through cooler 12 to the extraction column 1.

The above-referred-to need for water return can result when the amount of water which must be flashed The overall T.E.A. to $H_3PO_4$ mole ratios in the extractant and extract, respectively, are 0.72 and 0.8. The corresponding salt to water mole ratios are 0.43 (extractant) and 0.22 (extract). The volume ratio of feed to extractant is about 3:1.

The 3:1 volume ratio of feed to extractants employed in the preceding example is presently considered optimal but ratios of from about 2.5 to about 3.5 are considered highly satisfactory for the continuous, counter-current mode of operation illustrated.

The relative compositions given for the several streams in Table 5 are presently considered about optimal. However, the advantages of the continuous cyclic process illustrated in the latter example can be realized within a range of from about 0.97 to about 1.03 times the values given in the table.

Control of Extractant Regeneration

The percentages of the extracted T.E.A. and water recovered in a flash operation as per the preceding example depend on the flash temperature—which can range from about 90° to about 96° C. Once the desired composition for a particular bottoms (regenerated extractant) has been determined, the pH of the bottoms may be utilized for control of the flash temperature. If the pH is below the proper value, too much amine/acid salt is being dissociated and the flash temperature (steam flow through the preheater) should be reduced. If the pH is too high, the steam flow (or temperature) should be increased.

For any given amine, the dependency of pH on the relative amounts of the amine, water and $H_3PO_4$ can readily be determined. The values given in Table 6, below, for T.E.A., are illustrative.

TABLE 6 pH VERSUS COMPOSITION

| pH | Free H$_3$PO$_4$ | T.E.A./H$_3$PO$_4$ 1:1 Salt | Water | Solvent (Acetone/CH$_2$Cl$_2$) |
|---|---|---|---|---|
| 2.5 | 20.3 | 55.1 | 20.6 | 4.0 |
| 3.0 | 17.5 | 58.5 | 20.0 | 4.0 |
| 4.0 | 11.5 | 65.9 | 18.6 | 4.0 |
| 4.5 | 8.5 | 69.2 | 18.3 | 4.0 |

What is claimed is:

1. The process for removing an amine from a feed solution thereof in an organic solvent which comprises:
   (1) intimately contacting said feed with an extractant which is an aqueous solution of a 1:1 salt of said amine with ortho phosphoric acid and then separating the resultant raffinate and extract, and
   (2) liberating the extracted amine by heating the extract.

2. The process of claim 1 in which the feed also contains water and at least a substantial proportion of that water is co-extracted with the amine by the extractant.

3. The process of claim 1 in which the extractant also contains up to 1 mole of free H$_3$PO$_4$ per mole of the 1:1 salt.

4. The process of claim 2 in which said amine is triethylamine.

5. The process of claim 4 in which said organic solvent is a mixture of acetone and methylene chloride and the extractant also contains up to 1 mole of free H$_3$PO$_4$ per mole of the 1:1 salt.

6. The process of claim 5 in which the weight ratio of acetone to methylene chloride in said solvent is within the range of from about 72/28 to about 74/26.

7. The process of either claim 4 or claim 6 additionally comprising liberating water from said extract by heating it.

8. The process of claim 7 in which:
   a. said heating is continued until as much triethylamine as was extracted and at least as much water as was extracted are liberated from the extract,
   b. if necessary, as much water is added to the amine- and water-depleted extract as may be required to reestablish therein the water-to-salt ratio in the fresh extractant, and
   c. the aqueous salt and acid solution is reused to extract triethylamine and water from more of the feed solution.

9. The process of claim 5 in which:
   a. said feed solution consists of acetone, methylene chloride, triethylamine and water in mole percent amounts totaling to 100 and falling within respective ranges of from about 0.97 to about 1.03 times the following percentages: acetone 51.43, CH$_2$Cl$_2$ 13.01, water 34.70 and triethylamine 0.87,
   b. said extractant solution consists of acetone, methylene chloride, water, the 1:1 salt of triethylamine and H$_3$PO$_4$ and free H$_3$PO$_4$, in mole percent amounts totaling to 100 and falling within respective ranges of from about 0.97 to about 1.03 times the following percentages: acetone 4.12, CH$_2$Cl$_2$ 0.97, water 59.39, 1:1 salt 25.55 and H$_3$PO$_4$ 9.97,
   c. the feed and extractant are continuously charged, in a volume ratio of from about 2.5 to about 3.5, to an extraction column having an efficiency equivalent to that of at least six ideal extraction stages,
   d. said feed and extractant are counter-currently equilibrated in said column at a temperature of 30°±5° C. and are respectively converted therein to raffinate and extract phases which have the following compositions and are continuously withdrawn from the column in corresponding amounts;
      raffinate; acetone, methylene chloride and water in mole percent amounts totaling to 100 and falling within respective ranges of from about 0.97 to about 1.03 times the following percentages; acetone 66.32, CH$_2$Cl$_2$ 16.77 and water 16.92,
      extract; acetone, methylene chloride, water, 1:1 triethylamine H$_3$PO$_4$ and free H$_3$PO$_4$ in mole percent amounts totaling to 100 and falling within respective ranges of from about 0.97 to about 1.03 times the following percentages; acetone 7.16, CH$_2$Cl$_2$ 1.78, water 71.71, 1:1 salt 15.49 and H$_3$PO$_4$ 3.86,
   e. am amount of triethylamine equal to the amount extracted from said feed and an amount of water at least equal to the amount extracted from the feed are removed from the extract by preheating the extract to a temperature of from about 90° to about 96° C. and flashing it to atmospheric pressure,
   f. if necessary, as much water is added to the flash bottoms as may be required to reestablish the water to salt ratio the fresh extractant had, and
   g. the resulting aqueous salt and acid solution is re-used, as regenerated extractant, to extract triethylamine and water from more of said feed solution.

* * * * *

UNITED STATES PATENT AND TRADEMARK OFFICE
CERTIFICATE OF CORRECTION

PATENT NO. : 4,326,082
DATED : April 20, 1982
INVENTOR(S) : Patrick H. Martin and Stephen L. Michaels It is certified that error appears in the above—identified patent and that said Letters Patent is hereby corrected as shown below:

Column 1, line 17, interchange "only not" to read -- not only --;

Column 6, line 15, delete "1.1" and insert -- 1:1 --;

Column 6, line 18, after "(95 wt. %)" insert -- and water --;

Column 8, line 19, at the end of Table 2 insert -- Starting Feed Compositions in Table 1. --;

Column 11, line 62, "proportioning" has been misspelled;

Column 12, line 17, after "entering" delete "the" and insert -- and --.

Signed and Sealed this

Fifth Day of October 1982

[SEAL]

Attest:

GERALD J. MOSSINGHOFF

Attesting Officer

Commissioner of Patents and Trademarks